US00PP17215P2

(12) United States Plant Patent
Jonkers

(10) Patent No.: US PP17,215 P2
(45) Date of Patent: Nov. 14, 2006

(54) *DIASCIA* PLANT NAMED 'DALA LITPINK'

(50) Latin Name: *Diascia barberae*
Varietal Denomination: Dala Litpink

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/269,175

(22) Filed: Nov. 8, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP14,416 P2 * 12/2003 Talmadge ..... Plt./263
PP14,782 P2 * 5/2004 Stemkens ..... Plt./263

OTHER PUBLICATIONS

UPOV ROM GTITM Computer Database, GTI Jouve Retrieval Software 2005/05 Citations for 'Dala Litpink'.*

* cited by examiner

*Primary Examiner*—Wendy Haas
(74) *Attorney, Agent, or Firm*—Jondle & Associates P.C.

(57) ABSTRACT

A new *Diascia* plant particularly distinguished by large light pink flowers with deep pink markings, large medium green foliage with rounded leaves, a round, uniform, and medium-sized plant habit with dense branching and floriferousness is disclosed.

1 Drawing Sheet

Genus and species: *Diascia barberae.*
Variety denomination: 'Dala Litpink'.

BACKGROUND OF THE NEW PLANT

The present invention comprises a new and distinct cultivar of *Diascia*, botanically known as *Diascia barberae*, and hereinafter referred to by the cultivar name 'Dala Litpink'. The new cultivar originated from a hybridization made in 2003 in Andijk, The Netherlands. The female parent is a proprietary *Diascia* plant designated 'DSZ-39-8' (unpatented), having salmon-colored flowers and the male parent is a proprietary *Diascia* plant designated 'DSZ-41-3' (unpatented), having a lilac-rose flower color. The seeds produced by the hybridization were sown in May 2003, and the resulting seedlings were selected in July 2003. A single plant selection was chosen for further evaluation and for asexual propagation in the fall of 2003.

The new cultivar was created in 2003 in Andijk, The Netherlands and has been asexually reproduced repeatedly by vegetative cuttings and tissue culture micropropagation in Andijk, The Netherlands over a two-year period. The plant has also been trialed at Gilroy, Calif., and Andijk, The Netherlands. The present invention has been found to retain its distinctive characteristics through successive asexual propagations.

Plant Breeder's Rights for this cultivar were applied for in Europe on Jan. 24, 2005 and in Canada on Mar. 31, 2005.

SUMMARY OF THE INVENTION

The following are the most outstanding and distinguishing characteristics of this new cultivar when grown under normal horticultural practices in Gilroy, Calif. and Andijk, The Netherlands.

1. Large light pink flowers with deep pink markings;
2. Very floriferous with relatively short but numerous inflorescences;
3. Medium green foliage with relatively large, rounded leaves;
4. A medium-sized, round and uniform plant habit that is very densely branched; and
5. Early and continuous flowering throughout the summer.

DESCRIPTION OF PHOTOGRAPH

This new *Diascia* plant is illustrated by the accompanying photograph which shows blooms, buds, and foliage of the plant in full color; the colors shown are as true as can be reasonably obtained by conventional photographic procedures. The photograph is of three 6-month-old plants grown in a greenhouse with natural light in a spring trial setting.

The accompanying photograph shows blooms, buds, mature foliage, and plant habit; the inset shows mature inflorescences and buds.

DESCRIPTION OF THE NEW CULTIVAR

The following detailed descriptions set forth the distinctive characteristics of 'Dala Litpink'. The data which define these characteristics were collected from asexual reproductions carried out in Hillscheid, Germany. The plant history was taken on seven-month-old plants grown in 35-cm-diameter baskets (capable of holding 5-liters of soil) in an outdoor trial field under poly-cover rain protection. Color readings were taken under natural light. Color references are primarily to The R.H.S. Colour Chart of The Royal Horticultural Society of London (R.H.S.) (2001 edition). Texture description details were observed under a magnifying glass.

DESCRIPTION OF THE NEW PLANT

Classification:

*Family.*—Scrophulariaceae.

*Botanical name.*—*Diascia barberae* Hook.

Parentage:

*Female parent.*—'DSZ-39-8' a proprietary salmon-colored *Diascia* plant (unpatented).

*Male parent.*—'DSZ-41-3' a proprietary lilac-rose *Diascia* plant (unpatented).

Growth:

*Form and growth habit.*—Semi-trailing, rounded and very well branched.

*Height.*—20 cm (from top of soil) for 7-month-old plants to 40 cm (total vertical height) of a plant in a hanging basket.

*Width.*—70 cm for a 7-month-old plant.

*Spread* (*including flowers*).—59 cm, from the base of the main stem to the tips of the branches.

*Time to produce a finished flowering plant.*—About 10 weeks for a 5-inch pot.

*Outdoor plant performance.*—Plant in full sun; is free-flowering through the summer; has some heat tolerance; use in mixed container planting or mass planting in a bed.

*Time to initiate and develop roots.*—About 20 days in the spring.

*Root description.*—Fibrous and freely branching.

Leaves:

*Arrangement.*—Single and opposite.

*Shape.*—Cordate.

*Apex.*—Obtuse.

*Base.*—Cordate.

*Margin.*—Very shallow serrations.

*Immature.*—Color: Upper surface: RHS 137D. Lower surface: RHS 138B. Texture: Covered with very fine pubescence.

*Mature* (*fully expanded*).—Length: 2.2–2.5 cm. Width: 2.0–2.1 cm. Color: Upper surface: RHS 137A. Lower surface: RHS 138B.

*Venation.*—Type: Pinnate. Color: RHS 144B.

*Texture.*—Smooth and glossy.

*Petiole.*—Length: 0.2–0.3 cm. Width: 0.2 cm. Color: RHS 144A.

Stems:

*Length.*—Up to 45 cm without the inflorescence.

*Diameter.*—0.3 cm as measured in the middle (is square not round).

*Internode length.*—1.5–2.5 cm.

*Color.*—RHS 143A.

*Texture.*—Appears glabrous but has sparse pubescence.

*Anthocyanin.*—Absent.

Flower bud:

*Shape.*—Round and flattened.

*Diameter.*—0.7 cm.

*Length.*—0.4 cm.

*Color* (*at tight bud*).—RHS 65C with RHS 58B at the base.

Inflorescence:

*Inflorescence type.*—Terminal raceme with flowers in an alternate arrangement.

*Blooming habit.*—Continuously throughout the summer.

*Quantity of inflorescences per plant.*—100.

*Lastingness of individual blooms on the plant.*—3–4 days.

*Fragrance.*—None.

*Inflorescence length.*—8 cm.

*Penduncle.*—Color: RHS 143A (grass-green). Length: 7.5–8.0 cm. Diameter: 0.2 cm or less. Texture: Covered with fine hair.

Flower:

*Type.*—Single, zygomorphic; 5-lobes fused at the base.

*Quantity* (*per raceme*).—About 14 flowers and buds; solitary at a distance of approximately 0.5 to 1.2 cm; usually 5 to 6 open flowers at the same time.

*Shape.*—Salver-shaped.

*Length.*—2.3 cm.

*Depth.*—0.5 cm.

*Width.*—2.3 cm.

*Color.*—Upper surface: RHS 65B. Lower surface: Near RHS 65B. Corolla (inside color): Relatively weak RHS N57C (purple-pink); upper petals have a patch of RHS 12A (yellow) at the base.

*Petals* (*lobes*).—Quantity: 5. Arrangement: Two upper lobes (mainly fused) with two lateral lobes and one lower lobe. Apex: Rounded. Base: Fused. Margin: Entire. Texture: Smooth, papillose.

*Upper lobes, size.*—Length (from the Corolla opening): 0.6 cm. Width: 1.3 cm.

*Lateral lobes, size.*—Length (from the Corolla opening): 0.6 cm. Width: 0.8 cm. Spur: Shape: Funnel-shaped with a somewhat curved/bent end. Length: 0.7 cm. Diameter: 0.3 cm. Color: RHS 68B (pink).

*Lower lobe.*—Length (from the Corolla opening): 1.4 cm. Width: 1.8 cm.

*Sepals.*—Quantity: 5. Color: RHS 141B. Length: 0.25 cm. Width: 0.1 cm. Shape: Lanceolate. Apex: Acute. Base: Fused. Anthocyanin: Absent. Texture: Pubescent.

*Pedicels.*—Color: RHS 146A to RHS 148A. Length: 1.5 cm. Diameter: 0.1 cm. Texture: Pubescent (very fine).

Reproductive organs:

*Stamens.*—Quantity: 4; coherent, arching towards and somewhat twisting around the pistil. Filament: Color: RHS N77B (dull purple). Length: 0.3 cm. Diameter: 0.1 cm. Anther color: RHS 13D. Pollen amount: Abundant. Pollen color: RHS 13A.

*Pistils.*—Quantity: 1. Length: 0.4 cm. Stigma color: RHS 143D (light green). Style color: RHS 145C.

Fruit and seed set: Has not been observed.

Disease and insect resistance: Has not been observed.

COMPARISON WITH PARENTAL AND COMMERCIAL CULTIVARS

'Dala Litpink' differs from the female parent, proprietary *Diascia* plant 'DSZ-39-8' (unpatented), in that 'Dala Litpink' has light pink flowers, while 'DSZ-39-8' has salmon-colored flowers. Additionally, 'Dala Litpink' has a more compact and stronger branching habit than 'DSZ-39-8'.

'Dala Litpink' differs from the male parent, proprietary *Diascia* plant 'DSZ-41-3' (unpatented), in that 'Dala Litpink' has light pink flowers, while 'DSZ-41-3' has lilac-rose flowers. Additionally, 'Dala Litpink' has a rounder leaf shape and a more upright plant habit than 'DSZ-41-3'.

'Dala Litpink' differs from the commercial cultivar 'Diastara' (U.S. Plant Pat. No. 14,782) in that 'Dala Litpink' has larger flowers and deeper green foliage than 'Diastara'. Additionally, 'Dala Litpink' has light-pink petal lobes with a deeper bluish-pink inner color, while 'Diastara' has nearly white petal lobes with a reddish-pink inner color.

I claim:

1. A new and distinct cultivar of *Diascia* plant as shown and described herein.

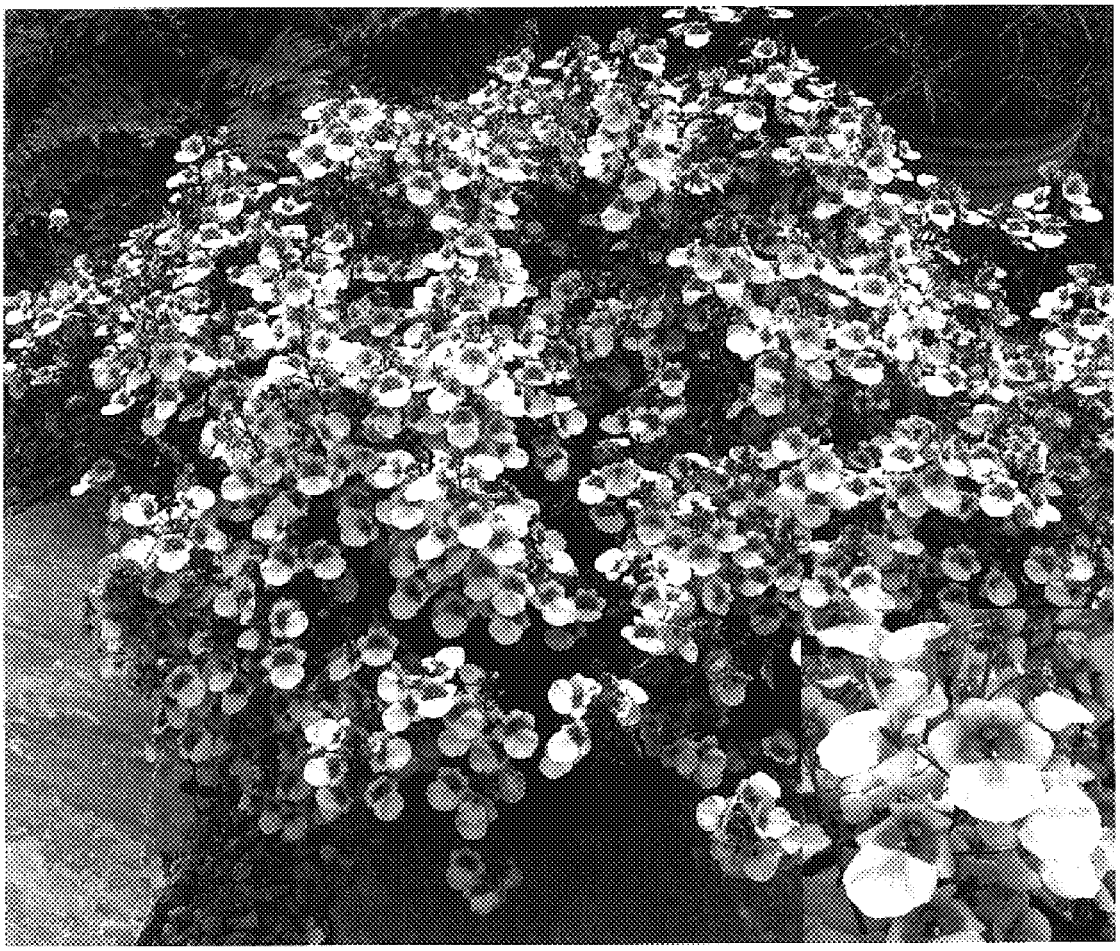

* * * * *